United States Patent
Li

(10) Patent No.: US 8,538,217 B2
(45) Date of Patent: Sep. 17, 2013

(54) LIGHT EMITTING DIODE LIGHTING SYSTEM

(75) Inventor: Yi-Qun Li, Danville, CA (US)

(73) Assignee: Intematix Corporation, Fremont, CA (US)

( * ) Notice: Subject to any disclaimer, the term of this patent is extended or adjusted under 35 U.S.C. 154(b) by 26 days.

(21) Appl. No.: 12/726,201

(22) Filed: Mar. 17, 2010

(65) Prior Publication Data

US 2010/0188867 A1 Jul. 29, 2010

Related U.S. Application Data

(62) Division of application No. 11/827,890, filed on Jul. 13, 2007, now abandoned.

(60) Provisional application No. 60/901,837, filed on Feb. 12, 2007.

(51) Int. Cl.
*G02B 6/04* (2006.01)
*F21V 7/04* (2006.01)

(52) U.S. Cl.
USPC ........... 385/120; 385/901; 362/556; 362/610; 362/612; 362/614

(58) Field of Classification Search
None
See application file for complete search history.

(56) References Cited

U.S. PATENT DOCUMENTS

| | | | |
|---|---|---|---|
| 3,290,255 A | 12/1966 | Smith | |
| 3,593,055 A | 7/1971 | Geusic et al. | |
| 3,670,193 A | 6/1972 | Thorington et al. | |
| 3,676,668 A | 7/1972 | Collins et al. | |
| 3,691,482 A | 9/1972 | Pinnow et al. | |
| 3,709,685 A | 1/1973 | Hercock et al. | |
| 3,743,833 A | 7/1973 | Martie et al. | |
| 3,763,405 A | 10/1973 | Mitsuhata | |
| 3,793,046 A | 2/1974 | Wanmaker et al. | |
| 3,819,973 A | 6/1974 | Hosford | |
| 3,819,974 A | 6/1974 | Stevenson et al. | |

(Continued)

FOREIGN PATENT DOCUMENTS

| | | |
|---|---|---|
| EP | 647694 | 4/1995 |
| EP | 1712165 A2 | 10/2006 |

(Continued)

OTHER PUBLICATIONS

CRC Handbook, 63rd Ed., (1983) p. E-201.

(Continued)

*Primary Examiner* — Hemang Sanghavi
(74) *Attorney, Agent, or Firm* — Vista IP Law Group, LLP

(57) ABSTRACT

A lighting system for generating an illumination product comprises an excitation source, blue/UV LED, operable to generate excitation radiation and a remotely located phosphor, photo luminescent material. Excitation radiation is guided from the excitation source to the phosphor by a waveguiding medium, the waveguiding medium being configured such that the distance the radiation travels from the excitation source to the phosphor layer is at least one centimeter in length. The UV/blue excitation source provides excitation radiation to the phosphor(s), causing the phosphor(s) to photo luminesce, and it may also provide a component of the final illumination product. The configuration of the waveguide allows a greater flexibility in lighting system configurations, such as hanging lighting fixtures, desk lighting fixtures, floor standing lighting fixtures, desk lamps, track lighting, spot lighting, accent lighting, lighting panels, inspection lamps and endoscopes.

16 Claims, 6 Drawing Sheets

(56) References Cited

U.S. PATENT DOCUMENTS

| | | | |
|---|---|---|---|
| 3,849,707 A | 11/1974 | Braslau et al. |
| 3,875,456 A | 4/1975 | Kana et al. |
| 3,932,881 A | 1/1976 | Mita et al. |
| 3,937,998 A | 2/1976 | Verstegen et al. |
| 3,972,717 A | 8/1976 | Wiedemann |
| 4,047,075 A | 9/1977 | Schoberl |
| 4,081,764 A | 3/1978 | Christmann et al. |
| 4,084,215 A | 4/1978 | Willenbrock |
| 4,104,076 A | 8/1978 | Pons |
| 4,143,394 A | 3/1979 | Schoberl |
| 4,176,294 A | 11/1979 | Thornton, Jr. |
| 4,176,299 A | 11/1979 | Thornton |
| 4,211,955 A | 7/1980 | Ray |
| 4,234,907 A | 11/1980 | Daniel |
| 4,305,019 A | 12/1981 | Graff et al. |
| 4,315,192 A | 2/1982 | Skwirut et al. |
| 4,443,532 A | 4/1984 | Joy et al. |
| 4,559,470 A | 12/1985 | Murakami et al. |
| 4,573,766 A | 3/1986 | Bournay, Jr. et al. |
| 4,618,555 A | 10/1986 | Suzuki et al. |
| 4,638,214 A | 1/1987 | Beers et al. |
| 4,667,036 A | 5/1987 | Iden et al. |
| 4,678,285 A | 7/1987 | Ohta et al. |
| 4,727,003 A | 2/1988 | Ohseto et al. |
| 4,772,885 A | 9/1988 | Uehara et al. |
| 4,845,223 A | 7/1989 | Seybold et al. |
| 4,859,539 A | 8/1989 | Tomko et al. |
| 4,915,478 A | 4/1990 | Lenko et al. |
| 4,918,497 A | 4/1990 | Edmond |
| 4,920,469 A | 4/1990 | Harding |
| 4,946,621 A | 8/1990 | Fouassier et al. |
| 4,992,704 A | 2/1991 | Stinson |
| 5,077,161 A | 12/1991 | Law |
| 5,110,931 A | 5/1992 | Dietz et al. |
| 5,126,214 A | 6/1992 | Tokailin et al. |
| 5,131,916 A | 7/1992 | Eichenauer et al. |
| 5,134,550 A | 7/1992 | Young |
| 5,143,433 A | 9/1992 | Farrell |
| 5,143,438 A | 9/1992 | Giddens et al. |
| 5,166,761 A | 11/1992 | Olson et al. |
| 5,208,462 A | 5/1993 | O'Connor et al. |
| 5,210,051 A | 5/1993 | Carter, Jr. |
| 5,211,467 A | 5/1993 | Seder |
| 5,237,182 A | 8/1993 | Kitagawa et al. |
| 5,264,034 A | 11/1993 | Dietz et al. |
| 5,278,731 A | 1/1994 | Davenport et al. |
| 5,283,425 A | 2/1994 | Imamura |
| 5,369,289 A | 11/1994 | Tamaki et al. |
| 5,405,709 A | 4/1995 | Littman et al. |
| 5,439,971 A | 8/1995 | Hyche |
| 5,518,808 A | 5/1996 | Bruno et al. |
| 5,535,230 A | 7/1996 | Abe |
| 5,557,168 A | 9/1996 | Nakajima et al. |
| 5,563,621 A | 10/1996 | Silsby |
| 5,578,839 A | 11/1996 | Nakamura et al. |
| 5,583,349 A | 12/1996 | Norman et al. |
| 5,585,640 A | 12/1996 | Huston et al. |
| 5,619,356 A | 4/1997 | Kozo et al. |
| 5,660,461 A | 8/1997 | Ignatius et al. |
| 5,677,417 A | 10/1997 | Muellen et al. |
| 5,679,152 A | 10/1997 | Tischler et al. |
| 5,763,901 A | 6/1998 | Komoto et al. |
| 5,770,887 A | 6/1998 | Tadatomo et al. |
| 5,771,039 A | 6/1998 | Ditzik |
| 5,777,350 A | 7/1998 | Nakamura et al. |
| 5,869,199 A | 2/1999 | Kido |
| 5,959,316 A | 9/1999 | Lowery |
| 5,962,971 A | 10/1999 | Chen |
| 5,998,925 A | 12/1999 | Shimizu et al. |
| 6,137,217 A | 10/2000 | Pappalardo et al. |
| 6,288,700 B1 * | 9/2001 | Mori ............... 345/102 |
| 6,299,338 B1 | 10/2001 | Levinson et al. |
| 6,340,824 B1 | 1/2002 | Komoto et al. |
| 6,350,041 B1 | 2/2002 | Tarsa et al. |
| 6,490,402 B1 * | 12/2002 | Ota ............... 385/147 |
| 6,504,301 B1 | 1/2003 | Lowery |
| 6,533,446 B2 | 3/2003 | Chen et al. |
| 6,576,488 B2 | 6/2003 | Collins et al. |
| 6,600,175 B1 | 7/2003 | Baretz et al. |
| 6,636,686 B1 | 10/2003 | Belfer |
| 6,642,618 B2 | 11/2003 | Yagi et al. |
| 6,642,652 B2 | 11/2003 | Collins et al. |
| 6,758,582 B1 | 7/2004 | Hsiao et al. |
| 6,814,470 B2 | 11/2004 | Rizkin et al. |
| 6,843,590 B2 | 1/2005 | Jones et al. |
| 6,851,834 B2 | 2/2005 | Leysath |
| 6,854,865 B2 | 2/2005 | Probst et al. |
| 6,869,812 B1 | 3/2005 | Liu |
| 6,893,140 B2 | 5/2005 | Storey et al. |
| 6,917,751 B2 | 7/2005 | Wang et al. |
| 6,921,920 B2 | 7/2005 | Kazakevich |
| 7,083,315 B2 | 8/2006 | Hansler et al. |
| 7,153,015 B2 | 12/2006 | Brukilacchio |
| 7,277,618 B2 | 10/2007 | Yamazaki et al. |
| 7,311,858 B2 | 12/2007 | Wang et al. |
| 7,390,437 B2 | 6/2008 | Dong et al. |
| 7,425,084 B2 | 9/2008 | Ruud et al. |
| 7,479,662 B2 | 1/2009 | Soules et al. |
| 7,505,655 B2 | 3/2009 | Yamazaki et al. |
| 7,506,986 B2 | 3/2009 | Koba et al. |
| 7,540,616 B2 | 6/2009 | Conner |
| 7,541,728 B2 | 6/2009 | Wang et al. |
| 7,575,697 B2 | 8/2009 | Li et al. |
| 7,601,276 B2 | 10/2009 | Li et al. |
| 7,615,795 B2 | 11/2009 | Baretz et al. |
| 7,628,513 B2 | 12/2009 | Chiu |
| 7,648,650 B2 | 1/2010 | Liu et al. |
| 7,655,156 B2 | 2/2010 | Cheng et al. |
| 7,762,701 B2 | 7/2010 | Luo et al. |
| 7,937,865 B2 * | 5/2011 | Li et al. ............... 40/542 |
| 7,943,945 B2 | 5/2011 | Baretz et al. |
| 7,955,878 B2 | 6/2011 | Harada |
| 7,976,206 B2 | 7/2011 | Wu et al. |
| 8,083,364 B2 | 12/2011 | Allen |
| 8,128,267 B2 | 3/2012 | Sormani et al. |
| 8,193,702 B2 | 6/2012 | Lenk et al. |
| 8,258,524 B2 | 9/2012 | Tan et al. |
| 2003/0042493 A1 | 3/2003 | Kazakevich |
| 2004/0016938 A1 | 1/2004 | Baretz et al. |
| 2005/0116597 A1 | 6/2005 | Hsu |
| 2005/0219171 A1 | 10/2005 | Gimbutas |
| 2005/0225988 A1 | 10/2005 | Chaves et al. |
| 2006/0012984 A1 | 1/2006 | Coushaine et al. |
| 2006/0049416 A1 | 3/2006 | Baretz et al. |
| 2006/0235277 A1 | 10/2006 | Ohkubo et al. |
| 2007/0145397 A1 | 6/2007 | Denbaars et al. |
| 2007/0279908 A1 | 12/2007 | Alcelik |
| 2007/0297190 A1 | 12/2007 | Ng |
| 2008/0049317 A1 | 2/2008 | Hara et al. |
| 2008/0075406 A1 | 3/2008 | Kadomi et al. |
| 2008/0158907 A1 | 7/2008 | Lin et al. |
| 2008/0224597 A1 | 9/2008 | Baretz et al. |
| 2008/0224598 A1 | 9/2008 | Baretz et al. |
| 2008/0262316 A1 | 10/2008 | Ajima et al. |
| 2009/0039756 A1 | 2/2009 | Yamamoto |
| 2009/0059359 A1 | 3/2009 | Nahm et al. |
| 2009/0067194 A1 | 3/2009 | Sanchez |
| 2009/0140630 A1 | 6/2009 | Kijima et al. |
| 2009/0251884 A1 | 10/2009 | Rains |
| 2010/0002444 A1 | 1/2010 | Konaka |
| 2010/0085737 A1 | 4/2010 | Yang |
| 2010/0149815 A1 * | 6/2010 | Erchak ............... 362/293 |
| 2010/0237760 A1 | 9/2010 | Yang |
| 2010/0308712 A1 | 12/2010 | Liu et al. |
| 2011/0006334 A1 | 1/2011 | Ishii et al. |
| 2011/0299284 A1 | 12/2011 | Van De Ven et al. |

FOREIGN PATENT DOCUMENTS

| | | |
|---|---|---|
| GB | 2 017 409 | 10/1979 |
| JP | S50-79379 | 11/1973 |
| JP | 60170194 | 9/1985 |
| JP | 862-189770 | 8/1987 |
| JP | H01-179471 | 7/1989 |
| JP | 01-260707 | 10/1989 |

| | | |
|---|---|---|
| JP | H02-91980 | 3/1990 |
| JP | H3-24692 | 3/1991 |
| JP | 4010665 | 1/1992 |
| JP | 4010666 | 1/1992 |
| JP | 04-289691 | 10/1992 |
| JP | 4-321280 | 11/1992 |
| JP | 05-152609 | 6/1993 |
| JP | 6207170 | 7/1994 |
| JP | 6-267301 | 9/1994 |
| JP | 6283755 | 10/1994 |
| JP | 07-099345 | 4/1995 |
| JP | H07-176794 | 7/1995 |
| JP | 07-235207 | 9/1995 |
| JP | H7-282609 | 10/1995 |
| JP | H08-7614 | 1/1996 |
| JP | 8-250281 | 9/1996 |
| JP | 2900928 | 3/1999 |
| JP | 2000275444 A | 10/2000 |
| JP | 2003515899 A | 5/2003 |
| JP | 2003162904 A | 6/2003 |
| JP | P2003-234513 | 8/2003 |
| JP | 2005150001 A | 11/2003 |
| JP | 2004229273 A | 8/2004 |
| JP | 2004287067 A | 10/2004 |
| JP | P3724490 | 9/2005 |
| JP | P3724498 | 9/2005 |
| JP | 2006037323 A | 2/2006 |
| JP | 2006253099 A | 9/2006 |
| JP | 2007155820 A | 6/2007 |
| TW | M253789 | 12/2004 |
| TW | M272411 | 8/2005 |
| TW | 200617449 | 6/2006 |
| WO | WO 9108508 | 6/1991 |
| WO | WO 2004099664 A1 | 11/2004 |
| WO | WO 2005101070 A1 * | 10/2005 |
| WO | WO 2006011571 A1 | 2/2006 |
| WO | WO 2006131924 A2 * | 12/2006 |

OTHER PUBLICATIONS

Lumogen® F Violet 570 Data Sheet; available at the BASF Chemical Company website Lumogen® F Violet 570 Data Sheet; available at the BASF Chemical Company website URL,http://worldaccount.basf.com/wa/EUen_GB/Catalog/Pigments/doc4/BASF/PRD/30048274/.pdt?title=Technicai%20Datasheet&asset_type=pds/pdf&language=EN&urn=urn:documentum:eCommerce_soi_EU :09007bb280021e27.pdf:09007bb280021e27.pdf.
Saleh and Teich, Fundamentals of Photonics, New York: John Wiley & Sons, 1991, pp. 592-594.
The Penguin Dictionary of Electronics, 3rd edition, pp. 315,437-438, 509-510, copyright 1979, 1988, and 1998.
LEDs and Laser Diodes, Electus Distribution, copyright 2001, available at URL:http://www.jaycar.com.au/images_uploaded/ledlaser.Pdf.
"Fraunhofer-Gesellschafl: Research News Special1997", http://www.fhg.de/press/md-e/md1997/sondert2.hlm,(accessed on Jul. 23, 1998), Jan. 1997, Publisher: Fraunhofer Institute.
Krames, M., et al., "Status and Future of High-Power Light-Emitting Diodes for Solid-Slate Lighting", "Journal of Display Technology", Jun. 2007, pp. 160-175, vol. 3, No. 2.
Kudryashov, V., et al., "Spectra of Superbright Blue and Green InGaN/AIGaN/GaN Light-Emitting diodes", "Journal of the European Ceramic Society", May 1996, pp. 2033-2037, vol. 17.
Lester, S., et al., "High dislocation densities in high efficiency GaN-based light-emitting diodes", "Appl. Phys. Lett.", Mar. 6, 1995, pp. 1249-1251, vol. 66, No. 10.
Mukai, T., et al., "Recent progress of nitride-based light emitting devices", "Phys. Stat. Sol.", Sep. 2003, pp. 52-57, vol. 200, No. 1.
Nakamura, S., et al., "High-power InGaN single-quantum-well-structure blue and violet light-emitting diodes", "Appl. Phys. Lett.", Sep. 25, 1995, pp. 1868-1870, vol. 67, No. 13.
Nakamura, S., et al., "The Blue Laser Diode: GaN Based Light Emitters and Lasers", Mar. 21, 1997, p. 239, Publisher: Springer-Verlag.
Nakamura, S., et al., "The Blue Laser Diode: The Complete Story, 2nd Revised and Enlarged Edition", Oct. 2000, pp. 237-240, Publisher: Springer-Verlag.

Mar. 22, 2012 Office Action in U.S. Appl. No. 12/131,119, issued by Steven Y. Horikoshi.
Pei, Q, et al., "Polymer Light-Emitting Electrochemical Cells", "Science", Aug. 25, 1995, pp. 1086-1088, vol. 269, No. 5227.
Dictionary Definition of Phosphor, Oxford English Dictionary Online, Mar. 9, 2012 (Only partial available due to corrupt file as provided by Examiner, Steven Y. Horikoshi, on Mar. 22, 2012 in U.S. Appl. No. 12/131,119; Request for Full Reference filed).
Feb. 21, 2012 Office Action in U.S. Appl. No. 12/131,118, issued by Abul Kalam.
Jan. 7, 2011 Office Action in U.S. Appl. No. 12/131,119, issued by Steven Y. Horikoshi.
May 4, 2010 Office Action in U.S. Appl. No. 12/131,119, issued by Examiner Steven Horikoshi.
Jul. 7, 2011 Office Action in U.S. Appl. No. 12/131,118, issued by Abu I Kalam.
Jul. 14, 2011 Office Action in U.S. Appl. No. 12/131,119, issued by Steve Horikoshi.
Aug. 26, 2010 Office Action in U.S. Appl. No. 12/131,118, issued by Examiner Abul Kalam.
Sep. 29, 2009 Office Action in U.S. Appl. No. 11/264,124, issued by Abu I Kalam.
Oct. 20, 2008 Office Action in U.S. Appl. No. 10/623,198, issued by Abu I Kalam.
Nov. 30. 2010 Office Action in U.S. Appl. No. 12/131/118. issued by Examiner Abu I Kalam.
Dec. 16. 2004 Office Action in U.S. Appl. No. 10/623,198, issued by Thao X. Le.
Jan. 29, 2007 Office Action in U.S. Appl. No. 10/623,198, issued by Thao X. Le.
Jan. 30, 2006 Office Action in U.S. Appl. No. 11/264,124, issued by Thao X. Le.
Feb. 4, 2005 Office Action in U.S. Appl. No. 10/623,198, issued by Thao X. Le.
Feb. 7, 2007 Office Action in U.S. Appl. No. 11/264,124, issued by Thao X. Le.
Feb. 26, 2008 Office Action in U.S. Appl. No. 11/264,124, issued by Abu I Kalam.
Mar. 2, 2009 Office Action in U.S. Appl. No. 10/623,198, issued by Abu I Kalam.
Mar. 4, 2011 Notice of Allowance, Notice of Allowability, Examiners Interview Summary, Examiners Amendment/Comment and Examiners Statement of Reason for Allowance in U.S. Appl. No. 11/264,124, issued by Abu I Kalam.
Mar. 7, 2008 Office Action in U.S. Appl. No. 10/623,198, issued by Abu I Kalam.
Mar. 28, 2006 Office Action in U.S. Appl. No. 10/623,198, issued by Thao X. Le.
Apr. 15, 2009 Office Action in U.S. Appl. No. 11/264,124, issued by Abu I Kalam.
Jun. 14, 2006 Office Action in U.S. Appl. No. 10/623,198, issued by Thao X. Le.
Jun. 26, 2007 Office Action in U.S. Appl. No. 10/623,198, issued by Thao X. Le.
Jul. 10, 2008 Office Action in U.S. Appl. No. 11/264,124, issued by Abu I Kalam.
Jul. 14, 2005 Notice of Allowance, Notice of Allowability, and Examiners Statement of Reasons for Allowance in U.S. Appl. No. 10/623,198, issued by Thao X. Le.
Aug. 21, 2006 Office Action in U.S. Appl. No. 10/623,198, issued by Thao X. Le.
Aug. 24, 2007 Office Action in U.S. Appl. No. 11/264,124, issued by Thao X. Le.
Sep. 17, 2009 Notice of Allowance, Notice of Allowability, Examiner's Amendmeni/Comment, and Examiner's Statement of Reasons for Allowance in U.S. Appl. No. 10/623,198, issued by Abul Kalam.
Amano, H., et al., "UV and blue electroluminescence from Al/GaN:Mg/GaN LED treated with low-energy electron beam irradiation (LEEBI)", "Institute of Physics: Conference Series", 1990, pp. 725-730, vol. 106, No. 10.
Roman. D., "LEDs Turn a Brighter Blue", "Electronic Buyers' News", Jun. 19, 1995, pp. 28 and 35, vol. 960, Publisher: CMP Media LLC.

Bradfield, P.L., et al., "Electroluminescence from sulfur impurities in a p-n. junction formed in epitaxial silicon", "Appl. Phys. Lett", 07110/1989, pp.•10D-102, vol. 55, No. 2.

Das, N.C., et al., "Luminescence spectra of ann-channel metal-oxide-semiconductor field-effect transistor at breakdown", 1990, pp. 1152-1153, vol. 56, No. 12.

Jang, S., "Effect of Avalanche-Induced Light Emission on the Multiplication Factor in Bipolar Junction Transistors", "Solid-State Electronics", 1991, pp. 1191-1196, vol. 34, No. 11.

Pavan, P., et al., "Explanation of Current Crowding Phenomena Induced by Impact Ionization in Advanced Si Bipolar Transistors by Means of . . . ", "Microelectronic Engineering", 1992, pp. 699-702, vol. 19.

Yang, Y., et al., "Voltage controlled two color light-emitting electrochemical cells", "Appl. Phys. Lett.", 1996, vol. 68, No. 19.

Zanoni, E., et al., "Measurements of Avalanche Effects and Light Emission in Advanced Si and SiGe Bipolar Transistors", "Microelectronic Engineering", 1991, pp. 23-26, vol. 15.

Zanoni, E., et al., "Impact ionization, recombination, and visible light emission in ALGaAs/GaAs high electron mobility transistors", "J. Appl. Phys.", 1991, pp. 529-531, vol. 70, No. 1.

Zhiming, Chen, et al., "Amorphous thin film white-LED and its light-emitting mechanism", "Conference Record of the 1991 International Display Research Conference", Oct. 1991, pp. 122-125.

Apr. 14, 2010 Office Action in U.S. Appl. No. 11/264,124.

Aug. 26, 2010 Office Action in U.S. Appl. No. 12/131,118.

Nov. 30, 2010 Office Action in U.S. Appl. No. 12/131,118.

Adachi, C. et al., "Blue light-emitting organic electroluminescent devices", "Appl. Phys. Lett.", Feb. 26, 1990, pp. 799-801, vol. 56, No. 9.

Akasaki, Isamu, et al., "Photoluminescence of Mg-doped p-type GaN and electroluminescence of GaN p-n. junction LED", "Journal of Luminescence", Jan.-Feb. 1991, pp. 666-670, vol. 48-49 pt. 2.

Amano, H., et al., "UV and blue electroluminescence from Al/GaN:Mg/GaN LED treated with low-energy electron beam irradiation (LEEBI)", "Institute of Physics: Conference Series", 1990, pp. 725-730, vol. 106.

Armaroli, N. et al., "Supramolecular Photochemistry and Photophysics.", "J. Am. Chern. Soc.", 1994, pp. 5211-5217, vol. 116.

Berggren, M., et al., "White light from an electroluminescent diode made from poly[3(4-octylphenyl)-2,2'-bithiophene] and an oxadiazole . . . ", "Journal of Applied Physics", Dec. 1994, pp. 7530-7534, vol. 76, No. 11.

Berggren, M. et al., "Light-emitting diodes with variable colours from polymer blends", "Nature", Dec. 1, 1994, pp. 444-446, vol. 372.

Boonkosum, W. et al., "Novel Flat Panel display made of amorphous SiN:H/SiC:H thin film LED", "Physical Concepts and Materials for Novel Optoelectronic Device Applications II", 1993, pp. 40-51, vol. 1985.

Chao, Zhang Jin, et al., "White light emitting glasses", "Journal of Solid State Chemistry", 1991, pp. 17-29, vol. 93.

Comrie, M. , "Full Color LED Added to Lumex's Lineup", "EBN", Jun. 19, 1995, p. 28.

Zdanowski, Marek, "Pulse operating up-converting phosphor LED", "Electron Technol.", 1978, pp. 49-61, vol. 11, No. 3.

Forrest, S. et al. , "Organic emitters promise a new generation of displays", "Laser Focus World ", Feb. 1995, pp. 99-107.

Hamada, Y. et al., "Blue-Light-Emitting Organic Electroluminescent Devices with Oxadiazole Dimer Dyes as an Emitter", "Jpn. J. Appl. Physics", Jun. 1992, pp. 1812-1816, vol. 31.

Hamakawa, Yoshihiro, et al., "Toward a visible light display by amorphous SiC:H alloy system", "Optoelectronics—Devices and Technologies", Dec. 1989, pp. 281-294, vol. 4, No. 2.

Hirano, Masao, et al., "Various performances of fiber-optical temperature sensor utilizing infrared-to-visible conversion phosphor", "Electrochemisty (JP)", Feb. 1987, pp. 158-164, vol. 55, No. 2, Publisher: Electrochemical Society of Japan.

El Jouhari, N., et al., "White light generation using fluorescent glasses activated by Ce3+, Tb3+ and Mn2+ ions", "Journal De Physique IV, Colloque C2", Oct. 1992, pp. 257-260, vol. 2.

Kido, J. et al. , "1,2,4-Triazole Derivative as an Electron Transport Layer in Organic Luminescent Devices", "Jpn. J. Appl. Phys. ", Jul. 1, 1993, pp. L917-L920, vol. 32.

Kido, J., et al., "White light-emitting organic electroluminescent devices using the poly(Nvinylcarbazole) emitter layer doped with . . . ", "Appl. Phys. Lett.", Feb. 14, 1994, pp. 815-817, vol. 64, No. 7.

Kido, J. et al. , "Bright blue electroluminescence from poly(N-vinylcarbazole)", "Appl. Phys. Letters", Nov. 8, 1993, pp. 2627-2629, vol. 63, No. 19.

Larach, S., et al., "Blue emitting luminescent phosphors: Review and status", "Int'l Workshop on Electroluminescence", 1990, pp. 137-143.

Maruska, H.P., et al., "Violet luminescence of Mg-doped GaN", "Appl. Phys. Lett.", Mar. 15, 1973, pp. 303-305, vol. 22, No. 6.

Maruska, H.P., "Gallium nitride light-emitting diodes (dissertation)", "Dissertation Submitted to Stanford University", Nov. 1973.

McGraw-Hill, "McGraw-Hill Dictionary of Scientific and Technical Terms, Third Edition", "McGraw-Hill Dictionary of Scientific and Technical Terms", 1984, p. 912 and 1446, Publisher: McGraw-Hill.

McGraw-Hill, "McGraw-Hill Encyclopedia of Science and Technology, Sixth Edition", "McGraw-Hill Encyclopedia of Science and Technology", 1987, p. 582 and 60-63, vol. 9-10, Publisher: McGraw-Hill.

Mimura, Hidenori, et al., "Visible electroluminescence from uc-SiC/porous Si/c-Si p-n. junctions", "Int. J. Optoelectron.", 1994, pp. 211-215, vol. 9, No. 2.

Miura, Noboru, et al., "Several Blue-Emitting Thin-Film Electroluminescent Devices", "Jpn. J. Appl. Phys.", Jan. 15, 1992, pp. L46-L48, vol. 31, No. Part 2, No. 1A 1B.

Muench, W.V., et al., "Silicon carbide light-emitting diodes with epitaxial junctions", "Solid-State Electronics", Oct. 1976, pp. 871-874, vol. 19, No. 10.

Pankove, J.I., et al., "Scanning electron microscopy studies of GaN", "Journal of Applied Physics", Apr. 1975, pp. 1647-1652, vol. 46, No. 4.

Sato, Yuichi, et al., "Full-color fluorescent display devices using a near-UV light-emitting diode", "Japanese Journal of Applied Physics", Jul. 1996, Page(s) L838-L839, vol. 35, No. ?A.

Tanaka, Shosaku, et al., "Bright white-light electroluminescence based on nonradiative energy transfer in Ce-and Eu-doped SrS thin films", "Applied Physics Letters", Nov. 23, 1987, pp. 1661-1663, vol. 51, No. 21.

Tanaka, Shosaku, et al., "White Light Emitting Thin-Film Electroluminescent Devices with SrS:Ce,Cl/ZnS:Mn Double Phosphor Layers", "Jpn. J. Appl. Phys.", Mar. 20, 1986, pp. L225-L227, vol. 25, No. 3.

Ura, M. , "Recent trends of development of silicon monocarbide blue-light emission diodes", "Kinzoku ", 1989, pp. 11-15, vol. 59, No. 9.

Werner, K. , "Higher Visibility for LEDs", "IEEE Spectrum", Jul. 1994, pp. 30-39.

Wojciechowski, J. et al. , "Infrared-To-Blue Up-Converting Phosphor", "Electron Technology", 1978, pp. 31-47, vol. 11, No. 3.

Yamaguchi, Y. et al., "High-Brightness SiC Blue LEDs and Their Application to Full Color LED Lamps", "Optoelectronics—Devices and Technologies", Jun. 1992, pp. 57-67, vol. 7, No. 1.

Yoshimi, Masashi, et al., "Amorphous carbon basis blue light electroluminescent device", "Optoelectronics—Devices and Technologies", Jun. 1992, pp. 69-81, vol. 7, No. 1.

Morkoc et al., "Large-band-gap SIC, 111-V nitride, and II-VI ZnSe-based semiconductor device technologies", J. Appl. Phys. 76(3), 1; Mar. 17, 1994; Illinois University.

Reexam Non-Final Office Action dated Sep. 20, 2010 for U.S. Appl. No. 90/010,940.

Reexam Non-Final Office Action dated Mar. 3, 2011 for U.S. Appl. No. 90/010,940.

Reexam Final Office Action dated Nov. 7, 2011 for U.S. Appl. No. 90/010,940.

Reexam Non-Final Office Action dated Jan. 26, 2012 for U.S. Appl. No. 90/010,940.

Reexam Final Office Action dated May 24, 2012 for U.S. Appl. No. 90/010,940.

Reexam Advisory Action dated Sep. 28, 2012 for U.S. Appl. No. 90/010,940.

Chinese Office Action and English Translation dated Dec. 19, 2011 for Chinese Appln. No. 200780051259.7.

Chinese Office Action and English Translation dated Jun. 11, 2010 for Chinese Appln. No. 200780051259.7.
Chinese Office Action and English Translation dated Oct. 8, 2012 for Chinese Appln. No. 200780051259.7.
Chinese Office Action and English Translation dated May 11, 2012 for Chinese Appln. No. 201010593209.5.
Japanese Office Action and English Translation dated Feb. 21, 2012 for Japanese Appln. No. 2009-549567.
Japanese Office Action and English Translation dated Jun. 19, 2012 for Japanese Appln. No. 2009-549567.
Taiwanese Office Action and English Translation and Search Report dated Jul. 23, 2010 for Taiwanese Appln. No. 96130925.
Taiwanese Office Action and English Translation dated Apr. 28, 2011 for Taiwanese Appln. No. 096130925.
Final Office Action dated Jul. 21, 2011 for U.S. Appl. No. 11/827,890.
Final Office Action dated May 27, 2010 for U.S. Appl. No. 11/827,890.
Non-Final Office Action dated Jun. 12, 2008 for U.S. Appl. No. 11/827,890.
Non-Final Office Action dated Nov. 15, 2011 for U.S. Appl. No. 11/827,890.
Non-Final Office Action dated Nov. 29, 2010 for U.S. Appl. No. 11/827,890.
Non-Final Office Action dated Sep. 24, 2009 for U.S. Appl. No. 11/827,890.
Notice of Allowance dated Jul. 25, 2012 for U.S. Appl. No. 11/827,890.
Non-Final Office Action dated Oct. 2, 2012 for U.S. Appl. No. 13/156,197.
Non-Final Office Action dated Feb. 19, 2013 for U.S. Appl. No. 12/726,194.
Non-Final Office Action dated Oct. 7, 2011 for U.S. Appl. No. 12/726,194.
Non-Final Office Action dated Jul. 24, 2012 for U.S. Appl. No. 12/726,194.
International Search Report and Written Opinion dated Jul. 28, 2008 for International PCT Application No. PCT/US07/16128, 15 pages.
International Search Report and Written Opinion dated Sep. 28, 2011 for International PCT Application No. PCT/US11/39862, 9 pages.
Foreign Office Action dated Mar. 5, 2013 for Japanese Appln. No. 2009-549567.
Foreign Office Action dated Jun. 13, 2013 for Chinese Appln. No. 200780051259.7.
Final Office Action dated May 3, 2013 for U.S. Appl. No. 13/156,197.

* cited by examiner

LIGHT EMITTING DIODE LIGHTING SYSTEM

CROSS REFERENCE TO RELATED APPLICATIONS

This application is a divisional of U.S. patent application Ser. No. 11/827,890, filed Jul. 13, 2007, entitled "Light Emitting Diode System" by Yi-Qun Li, which claims priority to U.S. Provisional Application Ser. No. 60/901,837 filed Feb. 12, 2007, entitled "Illumination systems comprising UV/blue excitation radiation waveguided to a remotely located phosphor," by Yi-Qun Li, which applications are incorporated by reference herein in their entirety.

BACKGROUND OF THE INVENTION

1. Field of the Invention

The field of the invention is directed to Light Emitting Diode (LED) lighting/illumination systems/fixtures or luminaires. More specifically, the present embodiments are directed to LED lighting systems with phosphor, photo luminescent, wavelength conversion to generate a desired color of light.

2. Description of the Related Art

The introduction of solid state semiconductor devices such as semiconductor light emitting diodes (LEDs) has allowed a new generation of energy efficient lighting systems to come into existence. Today, most lighting fixture designs utilizing LEDs comprise systems in which an LED (or an LED array) replaces conventional system components such as incandescent bulbs, mercury vapor and compact fluorescent lamps. LEDs often further include a phosphor, photo luminescent material, whose light, emitted in response to excitation radiation from the LED in the system, combines with light from the LED to produce the lighting system's illumination product. It is common in such conventional systems to incorporate further elements such as a light reflection backplane, a light diffusing front plane, and color filter pigments and paints.

U.S. Pat. No. 6,350,041 teaches a solid state lamp based on an LED which emits radially dispersed light for room illumination and other applications. The lamp comprises a solid state light source such as an LED or laser which transmits light through a separator to a disperser that disperses the light in a desired pattern and/or changes the color of light. In one embodiment, the light source comprises a blue emitting LED, the separator is a light pipe or fiber optic device and the disperser disperses the light radially and converts some of the blue light to yellow to produce a white light illumination product. The separator spaces the LED a sufficient distance from the disperser such that heat from the LED will not transfer to the disperser when the LED is carrying elevated currents as is necessary for room illumination. Such a lamp provides a solid state light source that can disperse light in many patterns, but is particularly applicable to a radial dispersion of white light for room illumination enabling the lamp to be used as an alternative light source in existing luminaires and lighting fixtures.

While such lighting system designs may have demonstrated properties that are acceptable to some customers, properties such as intensity, color temperature and color perception, for instance, they lack flexibility in how the design components may be placed in the system. Phosphor layers are typically placed, for example, adjacent or in close approximation to a light emitting surface of the LED die/chip from whom they derive their excitation energy. Often, the phosphor layer must be coated directly onto the LED die to achieve the desired intensity and color of the illumination being generated.

A need exists therefore for an improved illumination/lighting system based entirely on solid-state components, as before, but enhanced by providing greater flexibility in the placement of the components in the system.

SUMMARY OF THE INVENTION

Embodiments of the present invention are directed to lighting systems comprising an excitation radiation source, which may for example be an LED or a laser diode, and a remotely located phosphor(s). Light from the excitation source is transported to the phosphor via a waveguiding medium and provides excitation radiation to the phosphor(s) and/or phosphor layer(s), causing a photo luminescence. The light from the phosphor(s) may comprise the final illumination product, or it may be combined with any visible light from the radiation source (which may occur, for example, in the case of a blue LED as the radiation source). The final illumination product may be white light, or any colored light. The presence of the waveguide transporting excitation radiation (and possibly the blue light component of the final illumination product) to the phosphor(s) allows greater flexibility in the design of the lighting system. Lighting system configurations allowed by the presence of the waveguide include for example hanging lighting fixtures/luminaires, desk lighting fixtures, table lamps, wall sconces, floor standing lamps, track lighting, spot lighting, accent lighting, inspection light, endoscope light and/or panel lighting. Typically, the distance the radiation travels from the excitation source to the phosphor layer is at least one centimeter in length though it may be typically be 10 cm or more. In some embodiments, the peak emission wavelength of the light emitted by the blue/UV LED is greater than about 300 nm, and the peak emission wavelength of at least one component of the photo luminescent light emitted by the phosphor is greater than about 430 nm.

According to the invention a lighting system comprises: (a) an excitation source operable to generate excitation radiation; (b) a phosphor; and (c) a waveguide configured to guide the excitation radiation from the excitation source to the phosphor and wherein the configuration of the waveguide determines the configuration of the lighting system. The use of a waveguide enables new lighting system configurations and/or shapes to be fabricated since bulky components such as heat sinks, driver circuitry, and/or power converters can be located remote to the light emitting surface(s). To maximize light output a reflective surface can be provided on at least a part of at least one surface of the waveguide, the reflective surface being configured to reflect excitation radiation toward a light emitting surface of the waveguide. In one arrangement the distance the radiation travels from the excitation source to the phosphor layer is at least one centimeter in length, though it may typically travel 10, 50 or 100 cm in length.

In one arrangement the excitation source comprises a light emitting diode which is advantageously operable to emit UV/blue light, excitation radiation.

The waveguide can be configured to be in the shape of a lighting system such as a hanging lighting fixture, a desk lighting fixture, a floor standing lighting fixture, a desk lamp, track lighting, spot lighting, accent lighting or a lighting panel for incorporation into a suspended ceiling.

In one arrangement the phosphor is coated in layer form on at least a part of a light emitting surface of the waveguide, for example an end surface of an elongate waveguide. Alternatively, the phosphor is embedded in particulate form in at least a portion of the waveguide medium. Moreover, the light emitting surface of the waveguide can further includes a surface topology to enhance emission of light from the surface such as a roughening of the surface or a regular pattern.

The present invention finds particular application in lighting systems which produce a white light illumination product. The waveguide medium can comprise a glass, a plastics material such as acrylic or a polymeric resin.

In one arrangement the peak emission wavelength of the light emitted by the excitation source is greater than about 300 nm, and the peak emission wavelength of at least one component of the photo luminescent light emitted by the phosphor is greater than about 430 nm. Preferably, the peak emission wavelength of the light emitted by the excitation source is in a range from about 300 to about 500 nm, and at least one component of the photo luminescent light emitted by the phosphor is greater than about 500 nm.

To achieve a desired color of illumination product or color temperature the phosphor is a composition of at least two phosphors that emit light in the blue, green, yellow, orange, or red regions of the electromagnet spectrum.

According to a further aspect of the invention a method of generating a product illumination comprises: (a) generating excitation radiation from an excitation source; (b) waveguiding the excitation radiation to a phosphor configured to photo lumines upon absorption of at least some of the excitation radiation; and (c) emitting waveguided excitation radiation from the excitation source and photo luminescent light from the phosphor as a combined product illumination.

In one embodiment an endoscope lighting system comprises: (a) a light emitting diode operable to generate excitation radiation of a first wavelength; (b) a flexible fiber waveguide configured to guide the excitation radiation from the light emitting diode to a distal end of the fiber waveguide; and (c) a lens provided at the distal end of the waveguide, said lens incorporating a phosphor operable to emit light of a second wavelength in response to the excitation radiation.

According to a further embodiment a lighting panel comprises: (a) a plurality of light emitting diodes operable to generate excitation radiation of a first wavelength; (b) a substantially planar waveguide having a light emitting face; (c) a phosphor provided over substantially the entire light emitting face and (d) a reflecting layer provided on at least the surface of the waveguide opposite the light emitting face, the lighting panel being configured such that excitation radiation from the light emitting diodes is coupled into at least one edge of the waveguide such as to propagate substantially throughout the waveguide and is then emitted through the light emitting face where at least a part of the excitation radiation excites the phosphor which emits light of a second wavelength. Preferably, the lighting panel is configured to fit an aperture of a suspended ceiling. The lighting panel can further comprise a heat sink around at least a part of the edged of the waveguide, the heat sink being in thermal communication with the plurality of light emitting diodes.

According to a yet further embodiment a lighting system comprises: (a) at least one light emitting diode source operable to generate excitation radiation of a first wavelength; (b) a plurality of flexible optical fibers configured as a flexible sheet and each fiber having a phosphor on at least a part of its outer surface and (c) a flexible waveguide configured to couple excitation radiation from the excitation source to at least one end of each fiber such that the excitation radiation propagates substantially throughout the length of each fiber and is emitted through the light surface of each fiber and wherein at least a part of the excitation radiation excites the phosphor which emits light of a second wavelength. In one arrangement the fibers are woven as a flexible sheet and comprise the warp and/or weft of the sheet. Alternatively, the plurality of fibers can be mounted on a flexible backing material.

BRIEF DESCRIPTION OF THE DRAWINGS

In order that the present invention is better understood embodiments of the invention will now be described, by way of example only, with reference to the accompanying drawings in which.

DETAILED DESCRIPTION OF THE INVENTION

According to the present embodiments, a lighting system comprises three components: 1) an excitation source, typically a blue or UV emitting LED, 2) a remotely located phosphor, photo luminescent, material which may be coated as a layer on or incorporated in a system component, and 3) a waveguide media for transporting excitation radiation from the excitation source to the phosphor. In these embodiments the blue (e.g. 460 nm) emitting LED serves two purposes: one is to function as a source of excitation radiation needed to cause luminescence of the remotely located phosphor and the second is to contribute to the light which forms the final illumination product. The waveguide media can be either solid or liquid in form, but is most often solid to most efficiently guide or transport the excitation radiation. Simultaneously, the waveguide (or parts thereof) may carry the blue/UV light from the LED chip that is not absorbed by a phosphor, this light instead contributing to the illumination product formed by combining LED-originated light and phosphor-originated light.

The Shape of the Waveguide Can Determine the Configuration of the Lighting System The shape and/or configuration of the waveguide can determine, at least in part, the configuration and appearance that the present lighting system assumes. In some embodiments, the blue or UV-emitting LED chip may be embedded inside the waveguide media or positioned adjacent to the waveguide to ensure efficient coupling of the LED excitation radiation/light into the waveguide. The LED light may then be guided to a light output structure having a surface (external or internal) coated with the phosphor layer. The phosphor within this structure generates light with a desired emission-peak wavelength and the surface of the output structure is optimized for light extraction, by for example a surface topology such as a roughening of the surface. The presence of the waveguide allows for the lighting system to be configured in virtually any shape, allowing for highly efficient phosphor conversion, and the ability to aim the product illumination in a desired direction. The present lighting system further allows more convenient inclusion of a heat sink adjacent to the LED chip, since the output of the product illumination is located at a distant position. The color of the light delivered by the phosphor-coated output surface is controlled in part by the thickness and emission characteristics of the phosphor.

Description of Preferred Embodiments

Figure 1:
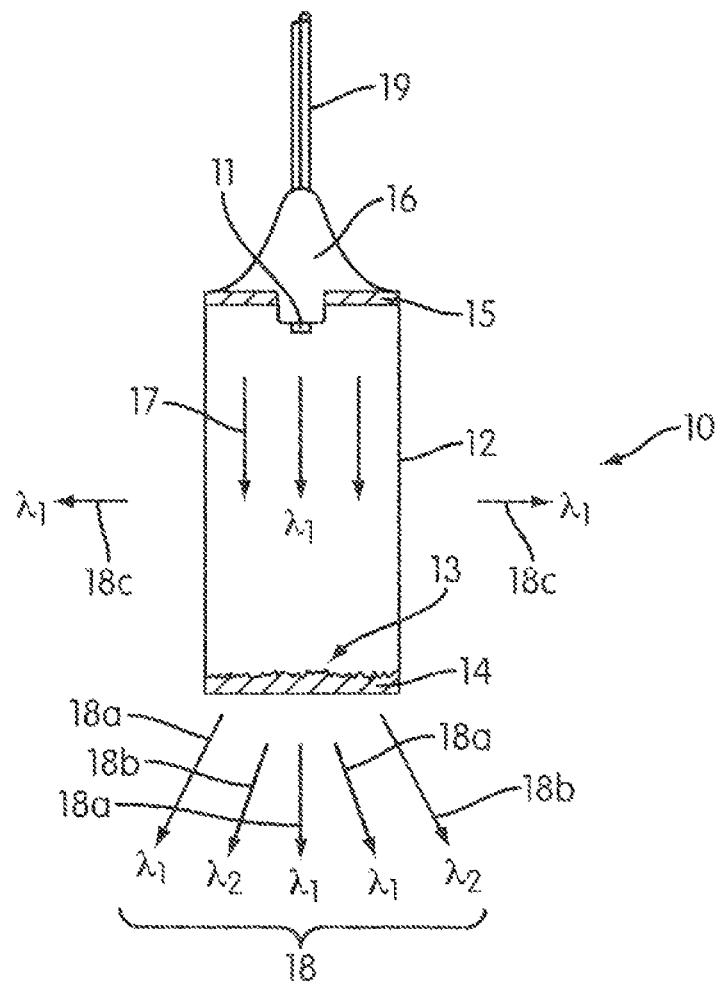
FIG. 1 is an illustration of one embodiment of the present invention wherein the lighting system comprises a hanging lighting fixture.

FIG. 1 is an illustration of one embodiment of the present invention in which the lighting system comprises a hanging lighting fixture 10. In this example, a blue (wavelength in a range 450 to 460 nm) or UV-emitting (soft UV 400 to 420 nm) LED 11 is mounted at a first end of a light waveguiding medium 12, which may be referred to as a "waveguide". The waveguide 12 can be fabricated from any material that is substantially transparent to the excitation radiation, blue/UV light, and can typically comprise a plastics material such as acrylic, butyrate or a glass. At an opposite end (distal end) of the waveguide 12 is a light output surface 13 of the waveguide, which in the embodiment illustrated is coated with a layer of the phosphor, photo luminescent, material 14. Examples of phosphor materials are given in table 1 below together with their CIE chromaticity coordinates CIE (x) and CIE (y). The phosphor can be applied as a layer using a binder material such as silicone gel. The first end of the waveguide may have a reflective surface 15 for directing light that strikes it back towards the output surface end 13 of the waveguide. The blue/UV LED 11 may be mounted on a heat sink 16, to absorb any excess heat produced by the LED. Additionally the heat sink 16 can be configured to support the fixture during installation and house a power supply to enable the fixture to be driven directly from a mains supply.

In operation light (excitation radiation) 17 emitted by the LED 11, which is of a first wavelength range $\lambda_1$, is guided by the waveguide 12 to the light emitting surface 13 where it causes excitation of the phosphor material 14 which re-emits light of a second longer wavelength range $\lambda_2$. Light 18 output from the second end of the waveguide which comprises the final illumination product is a combination of the emitted excitation radiation ($\lambda_1$) 18a and the light 18b emitted by the phosphor ($\lambda_2$). The illumination product 18 can be emitted in an isotropic manner, that is to say, in all directions; or it may be either fully focused or only partially focused depending on the configuration of the light emitting surface. The path length that the blue/UV light, excitation radiation, 17 travels along the waveguide 12, from the LED 11 to the phosphor layer 14 on the output surface 13, is typically at least one centimeter (cm), and in other embodiments may be greater than about 10 cm, 50 cm, or 100 cm. The lighting fixture 10 is suspended by a cable 19 used to additionally supply electrical power to the fixture. In FIG. 1, which is a schematic representation, the excitation radiation/light 17 is depicted as traveling in a straight line though it will be appreciated that in practice light will be guided by total internal reflection within the waveguide through a process of multiple internal reflections.

In the embodiment of FIG. 1, to aesthetically enhance the appearance of the lighting fixture, blue excitation light 18c is allowed to exit from the walls of the waveguide 12. In other embodiments the external surface of the waveguide 12: can be covered, partially or completely, with an opaque or reflective material to prevent emission of the excitation radiation; can be covered at least in part with one or more colored filters to impart a desired color to the emission 18c; or can have one or more phosphor materials provided on at least a part of the outer surface to generate a different color light 18c or the same color light as the product illumination 18.

Figure 2:
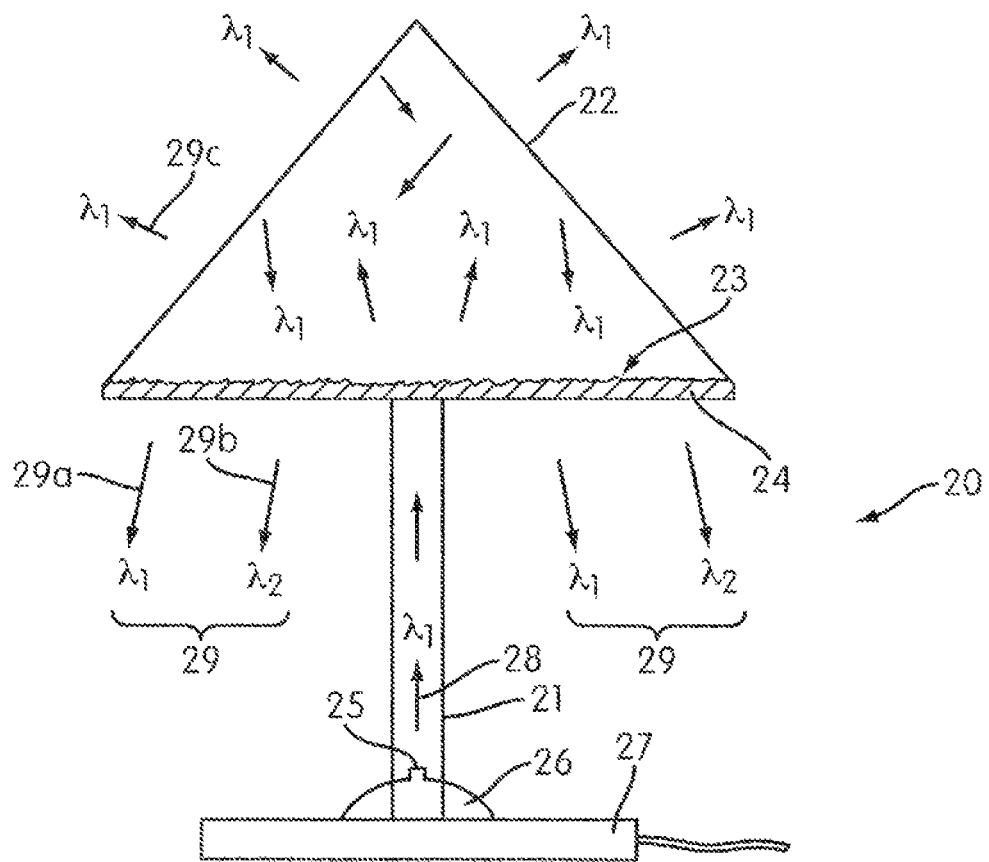
FIG. 2 is an illustration of another embodiment of the present lighting system, wherein the system comprises a desk lighting fixture or table lamp.

FIG. 2 is an illustration of another embodiment of a lighting system in accordance with the invention, wherein the system comprises a desk lighting fixture 20, desk or table lamp. Here, the waveguide media comprises two parts, a first part comprising a solid cylindrical rod 21 which is optically coupled to a base of a second part 22 which is shaped substantially as a solid-angle cone. The base of the cone forms the light output surface 23 of the waveguide. In this embodiment, the base of the cone 22 is coated with a phosphor layer 24. The blue/UV LED 25 is mounted at a distal end of the axial rod 21 which is positioned normal to the base of the cone 22, intersecting the base at its centre. As in the previous configuration, the LED 25 may be mounted on a heat sink 26 which itself is in thermal communication with a base 27.

In operation, blue/UV light 28 from the LED 25 travels up from the distal end of the rod shaped waveguide 21, through the waveguide 21, to the solid angle cone portion 22. Once inside the cone 22, the blue/UV light may be routed in various desired patterns, or it may be reflected off the curved surfaces of the cone in a diffuse manner, eventually striking the phosphor layer 24 covering the base of the cone. Visible blue light 29a from the blue/UV LED 25, and photo luminescent light from the phosphor(s) 29b in the coating, are emitted from the base of the cone, and in combination comprise the illumination product 29. The path length traveled by the blue/UV light through the waveguide, from the LED to the phosphor layer on the output surface, will vary depending on the number of reflections that occur on the surfaces of the cone portion of the waveguide. Again, the path length of the waveguide is at least one centimeter (cm), but in other embodiments may be greater than about 10 cm, 50 cm or 100 cm.

As with the hanging light fixture some blue excitation radiation 29c can be emitted through the curved surface of the cone shaped waveguide and/or rod shaped waveguide. As will be apparent to those skilled in the art, in other embodiments the external surface of one or both waveguide parts 21, 22: can be covered, partially or completely, with an opaque material to prevent emission of the excitation radiation; can be covered at least in part with one or more colored filters to impart a desired color to the emission 18c; or can have one or more phosphor materials provided on at least a part of the outer surface to generate a different color light 18c or the same color light as the product illumination 18. In another embodiment a patterned colored filter or colored phosphor pattern can be provided on the outer surface of one or more waveguides. In yet further embodiments the solid cone can be replaced with a hollow conical shell with an inner reflecting surface and the phosphor provided on a transparent/translucent window enclosing the open base of the cone.

Figure 3:
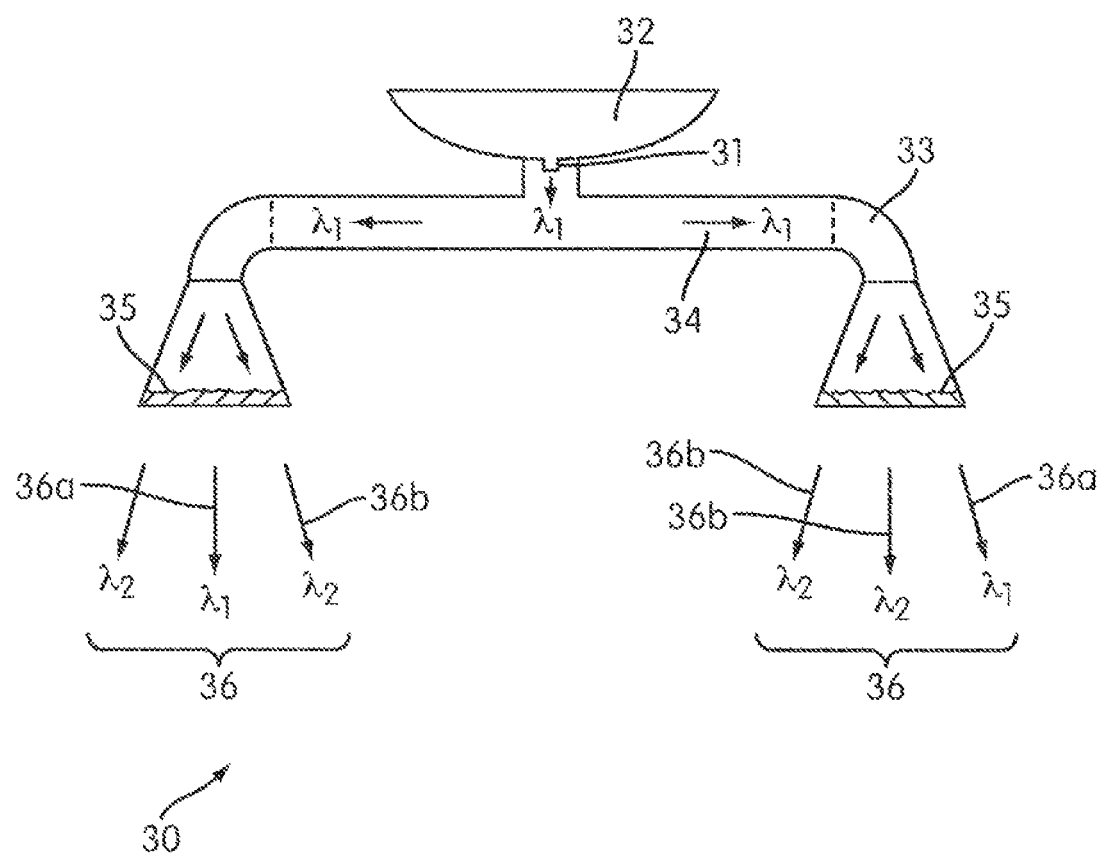
FIG. 3 is an illustration of another embodiment of the present invention, wherein the system comprises a spot lighting fixture.

FIG. 3 is an illustration of another embodiment of the present invention, wherein the system comprises what may be described as spot lighting, and/or accent lighting 30. Here again, the blue/UV LED 31 is mounted on a heat sink 32, some surfaces of which have been coated with a reflective material to maximize coupling of light into the waveguide. The waveguide 33 is configured to transport excitation light 34 according to a desired distribution pattern to a plurality of light output surfaces 35. The operation of the lighting system is analogous to the operation of the other embodiments and the illumination product 36 comprises the combined light from the LED 36a and phosphor 36b. To enable the light output to be directed in a desired direction the various parts of the waveguide 35 can be pivotally or flexibly coupled together.

Figure 4:
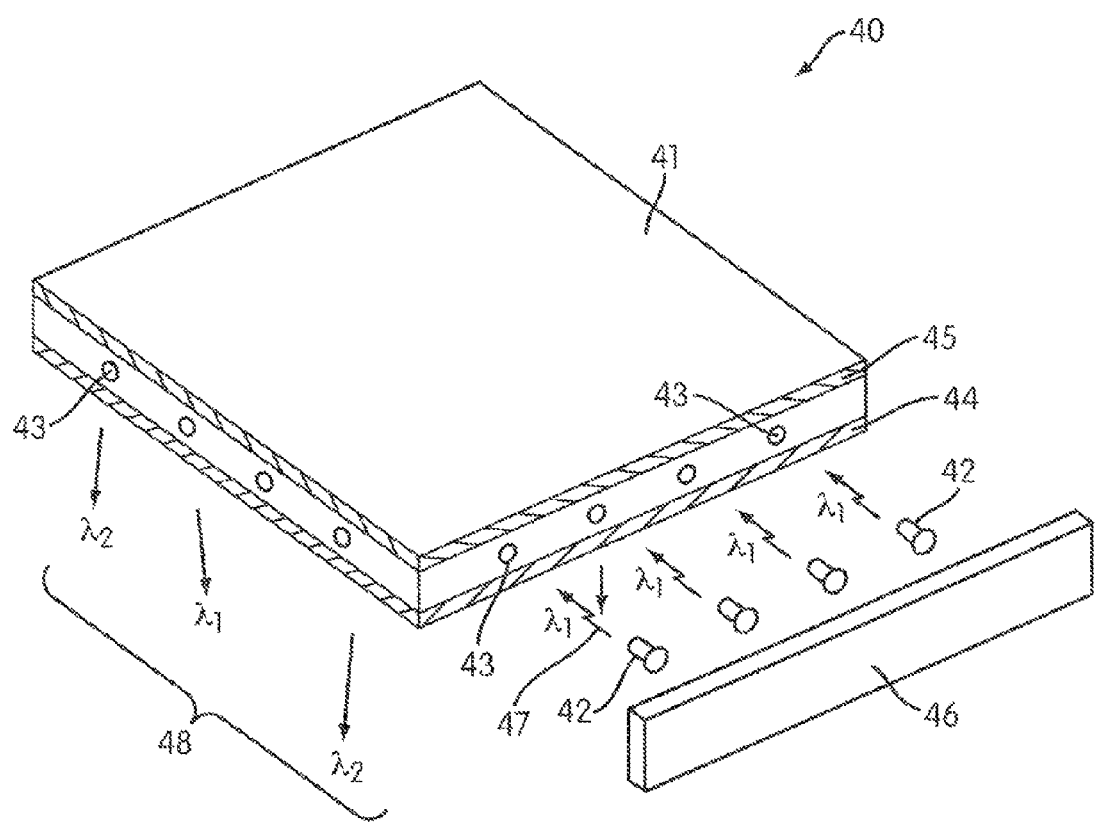
FIG. 4 is a partially exploded schematic representation of a lighting panel.

FIG. 4 is a partially exploded schematic representation of a lighting panel 40 in accordance with the invention. The example lighting panel is intended for use in a suspended (drop) ceiling of a type that are commonly used in offices and commercial premises in which a grid of support members (T bars) are suspended from the ceiling by steel cables and ceiling tiles supported by the grid of support members. The ceiling tiles can be square (60 cm×60 cm) or rectangular (4 feet×2 feet) in shape and fluorescent light fittings are configured to fit within such size openings.

In accordance with the invention the lighting panel comprises a square/rectangular sheet of waveguide material 41, which is dimensioned such that the lighting fixture, including heat sinks around the peripheral edge of the panel, will fit into a tile aperture of a standard suspended ceiling. A series of blue or UV-emitting LEDs 42 are mounted in corresponding apertures 43 within the edges of the planar waveguide 41. In the example illustrated LEDs 42 are provided along two orthogonal edges though in other embodiments they can be provided along one, two, three or all edges of the waveguide. The waveguide 41 can be constructed from any material which is substantially transparent to the excitation radiation and can typically comprise a sheet plastics material such as acrylic.

As illustrated, on a lower face of the planar waveguide 41 there is provided a layer of phosphor, photo luminescent, material 44. On the upper face of the planar waveguide 41, that is the face directed toward the supporting ceiling, there is provided a layer of highly reflective material 45 to ensure the majority of light is emitted from the lower face of the panel. The blue/UV LEDs 42 are mounted on a heat sink 46 (only one of which is illustrated in FIG. 4) which is configured along the edge of the lighting panel. To maximize light output the edges of the planar waveguide 41 can additionally include a reflecting surface.

In operation light (excitation radiation) 47 emitted by the LEDs 42, which is of a first wavelength range $\lambda_1$, is coupled into the waveguide 41 and is guided over the entire surface of the waveguide 41. Light which is emitted through the lower face causes excitation of the phosphor material 44 which re-emits light of a second longer wavelength range $\lambda_2$. Light 48 output from the lower face of the waveguide panel which comprises the final illumination product is a combination of the emitted excitation radiation ($\lambda_1$) 48a and the light 48b emitted by the phosphor ($\lambda_2$). Typically, the illumination product will be white light and the phosphor layer can comprise a mixture of green (525 to 535 nm) and orange (590 to 610 nm) emissive phosphors which are activated by blue light. The correlated color temperature (CCT), measured in degrees Kelvin, of light produced by the panel can be selected by the quantity, thickness, and composition of phosphor materials. In other arrangements the panel can be configured to produce colored light by appropriate selection of the phosphor material, thickness and excitation source.

To enhance the extraction of light, the surface of the waveguide panel advantageously includes some surface topology such as a roughening of the surface or a regular patterning of the surface. In alternative embodiments the phosphor can be incorporated within the waveguide medium in the form of suspended particles. An advantage of the lighting system of the invention is the compact nature, especially overall thickness, of the fixture which can be the same as the thickness of the planar waveguide. Although the lighting panel is described as being for use in a suspended ceiling it can also be used on a wall, flush with a ceiling, as a part of a floor or any horizontal surface such as a counter top or other planar surfaces such as stair treads or risers. Moreover, the panel can be used as a part of a structural component of a building or piece of furniture. In the case of stair treads or risers the wave waveguide preferably comprises a laminated glass construction with the phosphor being incorporated within one of the intervening laminations. In addition to flat panel lighting it will be appreciated that the waveguide can be fabricated into curved surfaces or other form as desired.

Figure 5:
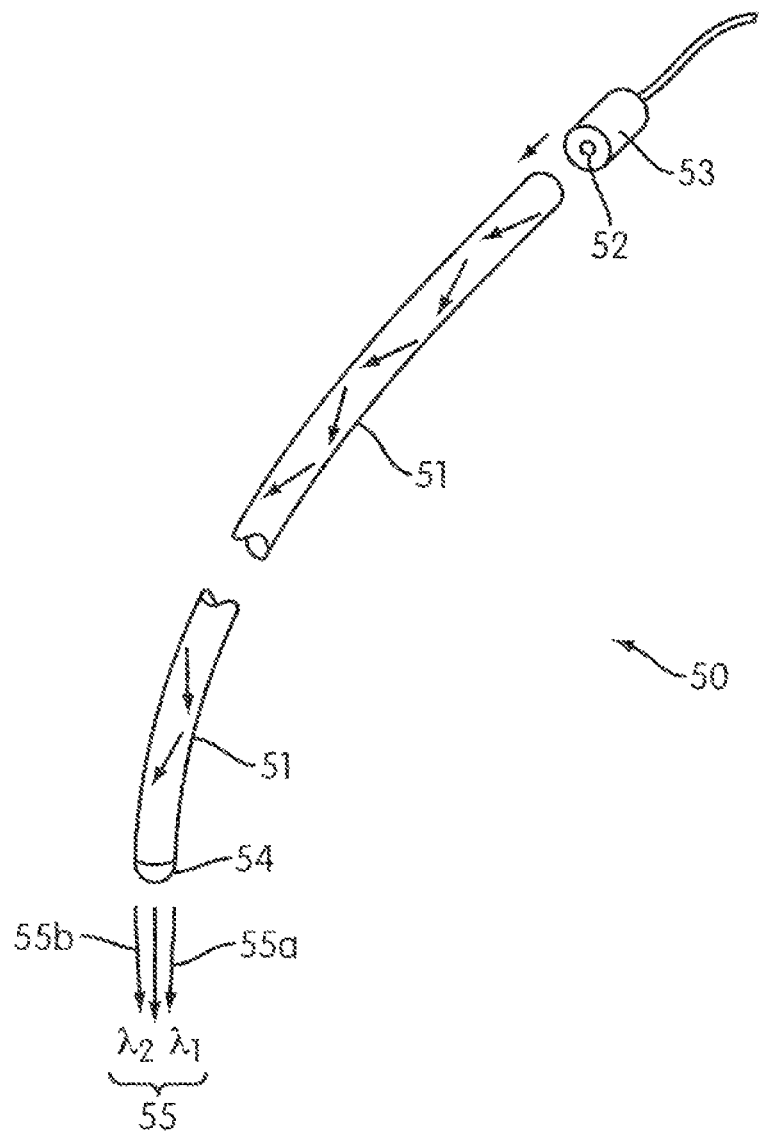
FIG. 5 is a schematic representation of an inspection light in accordance with the invention.

FIG. 5 is a schematic, partially exploded, illustration of another embodiment of the present invention, wherein the system comprises an inspection light 50 for use in applications where is access is limited and in which the light can be readily configured to provide illumination in a desired direction. Here the optical waveguide comprises a flexible optical fiber 51 which can include a resilient outer sheath to maintain the fiber in the desired configuration. A blue/UV LED 52 is mounted on a heat sink 35 that is configured to attach to the fiber 51 and couple light from the LED into the fiber. At a distal end of the fiber 51 a lens 54 incorporating the phosphor material is provided. The operation of the inspection light is analogous to the operation of the other embodiments and the illumination product 55 comprises the combined light from the LED 55a and phosphor 55b. The inspection light is particularly suited to applications where access is restricted or otherwise impaired and finds particular application as a light source in an endoscope or catheter (lumen) as used for example in keyhole surgery or as a dental inspection lamp which can be incorporated in a dentistry drill or other tool. In medical applications the lens can be detachable and replaced for each operation. In other embodiments the inspection light can also be mounted on a weighted base and the lamp them directed in a desired direction analogous to an angle poise desk lamp. Moreover, the base can provide thermal management of the LED by acting as a heat sink and can incorporate driver circuitry and/or AC to DC converter circuitry.

Figure 6:
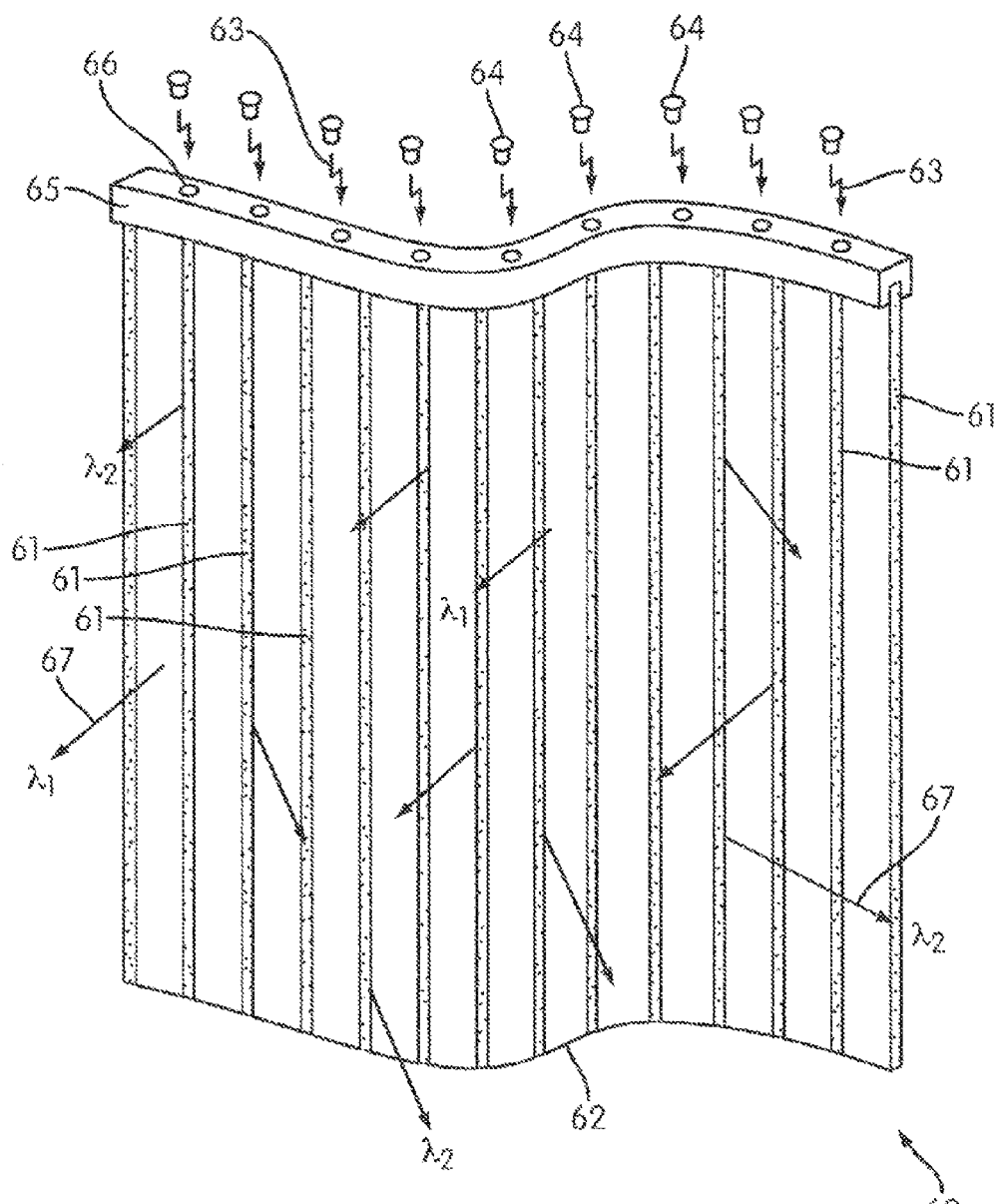
FIG. 6 is a representation of a lighting system in accordance with the invention comprising a flexible sheet.

Referring to FIG. 6 there is shown a further lighting system 60 in accordance with the invention which comprises a light emitting flexible sheet. In this embodiment the waveguide comprises a plurality of flexible optical fibers or filaments 61 which are attached to a flexible sheet backing material 62. The sheet material 62 can comprise any flexible material such as for example woven cloth, paper or a thin plastics material and can be transparent, translucent or opaque. Each fiber 61, which can comprise acrylic, has a phosphor coating on its outer surface (represented as a dotted pattern in FIG. 6) and in the example illustrated the fibers 61 are arranged in parallel although other patterns will be readily apparent to those skilled in the art such as a wavy pattern, zigzag etc. For ease of fabrication the fibers can have a circular cross section and can be fabricated by drawing a rod of material. In alternative arrangements they can have different cross sections such as for example elliptical or square. The fibers 61 are configured such that at least one end of each is accessible from a single edge of the material; as illustrated the ends of the fibers are accessible from the top and bottom edges.

Excitation energy 63 (of wavelength $\lambda_1$) from a plurality of blue LEDs 64 is coupled into the fibers 61 by a flexible light guide 65. The flexible light guide 65, which can be made of acrylic, can be molded onto the edge of the material/fibers 62/61 or include a slot for receiving the material/fibers. The LEDs 64 can be mounted in corresponding recesses 66, which as illustrated are in an upper surface of the flexible light guide 64 or molded as a part of the light guide 65. The LEDs are preferably low power to eliminate the need for heat sinking the LEDs. The flexible waveguide 65 further includes a reflecting layer on its upper and side faces to maximize light output from the lower face which is coupled into the fibers. Light output 66, illumination product, from the lighting system 60 can comprise a combination of the excitation radiation ($\lambda_1$) and light generated by the phosphor ($\lambda_2$).

Operation of the lighting system 60 is analogous to the operation of the other embodiments. Excitation radiation, light, 63 generated by the LEDs 64 is dispersed along the length of the light guide 65 and is coupled into the fibers 61 where it excites the phosphor as it propagates along the length of the fibers. The lighting system of the embodiment of FIG. 6 finds particular application as decorative or accent lighting and can be used for example as a drape curtain, wall hanging or a ceiling covering. Preferably the light emitting sheet material/fiber is manufactured in long lengths of standard width which can be cut to length and width and the flexible light guide 65 includes inter-cooperating plug and socket connectors to enable differing lengths of light guide to be produced in a modular fashion.

In a further embodiment the optical fibers 61 can be woven as part of a cloth in which the fibers comprise the warp and/or weft of the woven material. Alternatively, the cloth can be woven from fibers alone, though light would then need to be coupled into at least two edges of the material. Moreover, fibers coated in phosphors which emit different colors of light can be used to give a desired color pattern. Alternatively, the sheet material can be fabricated by laying the fibers over one another in a desired pattern and thermally bonding them together.

It will be appreciated that the present invention is not restricted to the specific embodiments described and that variations can be made that are within the scope of the invention. For example other lighting systems/fixtures/luminaires will be readily apparent to those skilled in the art by appropriate configuration of the waveguide such as for example a bollard lamp, wall sconces, chandeliers etc. To improve uniformity of the light output intensity the lighting system can further include a light diffusing material. In one arrangement this can be included within or on the light emitting surface of the waveguide.

A modular lighting system is also envisaged which comprises a set of cooperating waveguide members, such as splitters/dividers, straight, curved and flexible waveguide sections etc, which can then be used to construct different lighting systems as required.

Advantageously, the lighting system includes an LED chip having a peak emission wavelength greater than about 300 nm and preferably with a wavelength greater than 450 nm (blue) so that the excitation radiation can be used as a part of the illumination product.

In some embodiments the phosphor may be mixed into a host matrix that may comprise a paint or a resin, wherein the phosphor is impregnated into the host matrix at a concentration designed to impart to the product illumination the desired values of chromaticity, color rendering, temperature and intensity. At least a portion of a surface of the waveguide may be coated with the phosphor-containing host matrix. In other embodiments the phosphor may be blended in a polymeric or glass-based host matrix at a concentration such that at least a portion of the waveguide media is provided for by the phosphor-containing polymeric or glass-based host matrix.

The illumination product can be substantially white light in which case the LED chip has a peak emission wavelength greater than about 300 nm and a yellow or orange/green phosphor. The composition, amount, concentration, and distribution of the phosphor within or on the lighting system's output surface may be carefully controlled to achieve the desired color rendering of the product white light. Proper variation of those parameters will produce a white light that may appear substantially different, with as much bluish or yellowish character as the designer wishes.

TABLE 1

Examples of blue/UV activated phosphor, photo luminescent, materials.

| Color of emitted light | Chromaticity coordinates CIE (x) | CIE (y) | Phosphor composition |
|---|---|---|---|
| Green | 0.25 | 0.63 | $Sr_{0.925}Ba_{1.025}Mg_{0.05}Eu_{0.06}Si_{1.03}O_4Cl_{0.12}$ |
| Yellow | 0.41 | 0.56 | $Sr_{1.40}Ba_{0.55}Mg_{0.05}Eu_{0.06}Si_{1.03}O_4Cl_{0.12}$ |
| Yellow | 0.44 | 0.53 | $Sr_{1.6}Ba_{0.35}Mg_{0.05}Eu_{0.06}Si_{1.03}O_4Cl_{0.12}$ |
| Yellow | 0.46 | 0.51 | $Sr_{1.725}Ba_{0.225}Mg_{0.05}Eu_{0.06}Si_{1.03}O_4Cl_{0.12}$ |
| Yellow | 0.47 | 0.50 | $Sr_{1.725}Ba_{0.15}Mg_{0.05}Eu_{0.06}Si_{1.03}O_4Cl_{0.12}$ |
| Orange | 0.54 | 0.46 | $Sr_3Eu_{0.06}Si_{1.02}O_5F_{0.18}$ |
| Orange | 0.55 | 0.44 | $Sr_3Eu_{0.06}Si_{1.02}O_5F_{0.18}$ |
| Orange | 0.57 | 0.42 | $(Sr_{0.9}Ba_{0.1})_{2.76}Eu_{0.06}Si_{1.02}O_5F_{0.18}$ |

What is claimed is:

1. A lighting system comprising:
   a light emitting flexible sheet that comprises a plurality of flexible elongate light transmissive waveguides, each said flexible waveguide having a light emitting surface;
   at least one phosphor provided over at least a part of the light emitting surface of said flexible waveguide and
   a plurality of light emitting diodes, each said light emitting diode operable to generate blue excitation light having a peak emission wavelength greater than 450 nm,
   the lighting system being configured such that excitation light is coupled into the waveguides such that said excitation light propagates through said flexible waveguide and is then emitted through the light emitting surface and wherein at least a part of the excitation radiation excites the at least one phosphor which emits light of a different color, wherein the illumination product of the system is a combination of the excitation light and photo luminescent light emitted by the at least one phosphor.

2. The lighting system of claim 1, and further comprising a further light transmissive waveguide in optical communication with at least one end of each flexible waveguide and wherein excitation light is coupled into the further waveguide and is then coupled into each of the flexible waveguides.

3. The lighting system of claim 2, wherein the further waveguide is flexible.

4. The lighting system of claim 2 or claim 3, and further comprising a plurality apertures in at least one edge of the further waveguide and wherein each light emitting diode is mounted in a respective one of the apertures.

5. The lighting system of claim 1, wherein the at least one phosphor is provided as a layer on at least a part of the light emitting surface of each flexible waveguide.

6. The lighting system of claim 1, wherein the at least one phosphor is a composition of at least two phosphors.

7. The lighting system of claim 1, wherein the flexible waveguides comprise optical fibers.

8. The lighting system of claim 7, wherein the optical fibers have a cross section selected from the group consisting of: circular, elliptical and square.

9. The lighting system of claim 7, wherein the optical fibers are woven as a flexible sheet and comprise the warp and/or weft of the sheet.

10. The lighting system of claim 7, wherein the plurality of optical fibers are mounted on a flexible backing material.

11. The lighting system of claim 1, and further comprising a surface topology of the light emitting surface of the flexible waveguides, said topology being configured to enhance emission of light from the light emitting surface.

12. The lighting system of claim 11, wherein the surface topology is selected from the group consisting of: a surface roughening and a regular patterning.

13. The lighting system of claim 1, wherein the flexible waveguide is a medium selected from the group consisting of: a polymeric resin, an acrylic, a butyrate and a glass.

14. The lighting system of claim 1, wherein the peak emission wavelength of at least one component of the photo luminescent light emitted by the at least one phosphor is greater than about 500 nm.

15. The lighting system of claim 1, wherein the lighting system produces a white light illumination product.

16. The lighting system of claim 10, wherein the optical fibers are arranged in a pattern on the flexible backing material.

* * * * *